United States Patent
Haruta et al.

(10) Patent No.: US 6,362,209 B1
(45) Date of Patent: *Mar. 26, 2002

(54) HETEROCYCLIC AROMATIC OXAZOLE COMPOUNDS AND USE THEREOF

(75) Inventors: Junichi Haruta; Hiromasa Hashimoto; Mutsuyoshi Matsushita, all of Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/398,997

(22) Filed: Sep. 17, 1999

Related U.S. Application Data

(62) Division of application No. 08/693,051, filed as application No. PCT/JP95/02600 on Feb. 18, 1995, now Pat. No. 5,994,381.

(30) Foreign Application Priority Data

| Dec. 20, 1994 | (JP) | ............................................ | 6-335838 |
| Mar. 27, 1995 | (JP) | ............................................ | 7-93099 |
| Jun. 6, 1995 | (JP) | ............................................ | 7-164656 |
| Nov. 20, 1995 | (JP) | ............................................ | 7-326571 |

(51) Int. Cl.$^7$ .......................... A61K 31/42; A61P 29/00; C07D 263/30
(52) U.S. Cl. ....................... 514/374; 548/235; 548/236
(58) Field of Search .................. 514/374; 548/235, 548/236

(56) References Cited

U.S. PATENT DOCUMENTS

| 3,476,766 A | 11/1969 | Brown | 260/302 |
| 3,506,679 A | 4/1970 | Cavalla et al. | 260/302 |
| 3,546,342 A | 12/1970 | Brown | 424/270 |
| 3,574,228 A | 4/1971 | Brown | 260/307 |
| 3,901,908 A | 8/1975 | Fitzi et al. | 260/309 |
| 4,451,171 A | 5/1984 | Uffner et al. | 404/31 |
| 4,612,321 A | 9/1986 | Terao et al. | 514/338 |
| 4,632,930 A | 12/1986 | Carini et al. | 514/365 |
| 4,782,058 A | 11/1988 | Griffith | 514/250 |
| 4,822,805 A | 4/1989 | Takasugi et al. | 514/341 |
| 4,849,007 A | 7/1989 | Rempfler et al. | 71/76 |
| 4,894,083 A | 1/1990 | Rempfler et al. | 71/88 |
| 5,134,142 A | 7/1992 | Matsuo et al. | 514/255 |
| 5,219,731 A | 6/1993 | Sih | 435/18 |
| 5,380,738 A | 1/1995 | Norman et al. | 514/338 |
| 5,474,995 A | 12/1995 | Ducharme et al. | 514/241 |
| 5,536,752 A | 7/1996 | Ducharme et al. | 514/602 |
| 5,541,080 A | 7/1996 | Sih | 435/18 |
| 5,719,163 A | 2/1998 | Normal et al. | 514/311 |
| 5,994,381 A * | 11/1999 | Haruta et al. | 514/374 |
| 6,090,834 A | 7/2000 | Talley et al. | 514/374 |

FOREIGN PATENT DOCUMENTS

| EP | 0 117 578 | 9/1984 |
| GB | 1 206 403 | 9/1970 |
| GB | 2 123 830 | 2/1984 |
| GB | 2 123 831 | 2/1984 |
| JP | 57 183767 | 11/1982 |
| JP | 59 500054 | 1/1984 |
| JP | 59 500055 | 1/1984 |
| JP | 59 155365 | 9/1984 |
| JP | 60 058981 | 4/1985 |
| JP | 62 138485 | 6/1987 |
| JP | 2 083372 | 2/1990 |

(List continued on next page.)

OTHER PUBLICATIONS

T. Noh et al., J. Am. Chem. Soc., vol. 115, No. 8, "Photochemistry of α–(o–Tolyl)acetone and Some Derivatives: Triplet αa–Cleavage and Singlet o–Hydrogen Abstraction," pp. 3105–3110 (1993).

(List continued on next page.)

Primary Examiner—Brenda Coleman
(74) Attorney, Agent, or Firm—Foley & Lardner

(57) ABSTRACT

A heterocyclic aromatic oxazole compound of the formula (I)

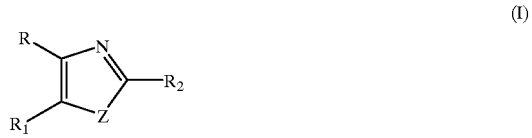

(I)

wherein Z is an oxygen atom; one of R and $R_1$ is a group of the formula

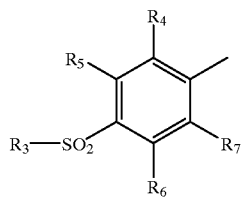

wherein $R_3$ is lower alkyl, amino or lower alkylamino, and $R_4$, $R_5$, $R_6$ and $R_7$ are the same or different and each is hydrogen atom, halogen atom, lower alkyl, lower alkoxy, trifluoromethyl, hydroxy or amino, provided that at least one of $R_4$, $R_5$, $R_6$ and $R_7$ is not hydrogen atom, and the other is an optionally substituted cycloalkyl, an optionally substituted heterocyclic group or an optionally substituted aryl; and $R_2$ is a lower alkyl or a halogenated lower alkyl, and a pharmaceutically acceptable salt thereof. The heterocyclic aromatic oxazole compound and pharmaceutically acceptable salts thereof have antipyretic action, analgesic action, anti-inflammatory action, and particularly, selective inhibitory action on cyclooxygenase-2 (COX-2), and are expected to be useful as anti-inflammatory agents with less side-effects such as digestive tract disorders.

8 Claims, No Drawings

FOREIGN PATENT DOCUMENTS

| JP | 3 116048 | 5/1991 |
|---|---|---|
| JP | 3 141 261 | 6/1991 |
| JP | 3 208056 | 9/1991 |
| JP | 5 45883 | 2/1993 |
| JP | 5 070446 | 3/1993 |
| WO | WO 91/19708 | 12/1991 |
| WO | 94 27980 | 2/1994 |
| WO | 94 15932 | 7/1994 |
| WO | WO 94/26731 | 11/1994 |
| WO | WO 96/36617 | 11/1996 |

OTHER PUBLICATIONS

S. Berk et al., J. Org. Chem., vol. 53, No. 24, "General Approach to Highly Functionalized Benzylic Organometallics of Zine and Copper," pp. 5789–5791 (1988).

P. Seemuth et al., J. Org. Chem., vol. 43, No. 154, "α–Hetero–Substituted Phosphonate Carbanions.7. Synthesis of Deoxybenzions and Benz[b]furans," pp. 3063–3065 (1978).

H. Bergs et al., Chemische Berichte, vol. 67, Zur Darstellung von α,β–ungesättigten cyclischen Ketonen und Keto–säuren (II. Mitteil.), pp. 1617–1623 (1934).

M. Artico et al., Eur. J. Med. Chem, vol. 28, "Antifungal agents.5. Chloro and amino derivatives of 1,2–diaryl–1–(1H–imidazol–1–yl)ethane with potent antifungal activities," pp. 715–720 (1993), Elsevier, Paris.

R. Moffett et al., J. of Medicinal Chem., vol. 15, No. 12, "Central Nervous System Agents.4.Analogs of 3–Amino–2–phenylpropiophenone," pp. 1243–1247 (1972).

A. Fischer et al., J. Amer. Chem. Soc., vol. 83, No. 19, "Dissociation Constants of the Conjugate Acids of Substituted Benzyl Phenyl Ketones and of Alkyl–substituted Benzophenones," pp. 4208–4210 (1961).

H. House et al., J. Org. Chem., vol. 28, No. 12, "The Neber Rearrangement of Substituted Desoxybenzoin Oxime Toxylates,"pp. 307–311 (1963).

C. Yokoyama et al. Biochem. Biophys. Res. Commun., vol. 165, No. 2, pp. 888–894 (1989) "Cloning of Human Gene Encoding Prostagladin Endoperoxide Synthase and Primary Structure of the Enzyme".

W. Smith et al. Biochim. Biophys. Acta., vol. 1083, pp. 1–17 (1991) "Prostaglandin endoperoxide synthase: structure and catalysis".

D. DeWitt Biochim. Biophys. Acta., vol. 1083, pp. 121–134 (1991) "Prostaglandin endoperoxide synthase: regulation of enzyme expression".

M. Holtzman et al. J. Biol. Chem., vol. 267, No. 30, pp. 21438–21445 (1992) "Identification of a Pharmacologically Distinct Prostaglandin H Synthase in Cultured Epithelial Cells".

W. Xie et al. Proc. Natl. Acad. Sci., USA, vol. 88, pp. 2692–2696 (1991) "Expression of a mitogen–responsive gene encoding prostaglandin synthase is regulated by mRNA splicing".

D. Kujubu et al. J. Bio. Chem., vol. 266, No. 20, pp. 12866–12872 (1991) "TIS10, a Phorbol Ester Tumor Promoter–inducible mRNA from Swiss 3T3 Cells, Encodes a Novel Prostaglandin Synthase/Cyclooxygenase Homologue".

T. Hla et al. Proc. Natl. Acad. Sci. USA, vol. 89, pp. 7384–7388 (1992) "Human cyclooxygenase–2 cDNA".

R. Brown J. Org. Chem., vol. 56, pp. 4974–4976 (1991) "A Convenient Method for the Preparation of (Alkysulfonyl) benzoic Acids".

S. Steglich et al. Chem. Ber., vol. 102, "Acylierung von Oxazolonen–(5) mit Carbonsäurehalogeniden, eine Erweiterung der Dakin–West–Reaktion," pp. 883–898 (1969).

G. Subba et al. Indian J. Chem., vol. 20B, pp. 322–323 (1981) "A Convenient Synthesis of 2,4,5–Trisubstituted Oxazoles".

* cited by examiner

HETEROCYCLIC AROMATIC OXAZOLE
COMPOUNDS AND USE THEREOF

CROSS REFERENCE TO RELATED
APPLICATIONS

This application is a divisional of U.S. application Ser. No. 08/693,051 filed Aug. 19, 1996, now U.S. Pat. No. 5,994,381, which is a national stage entry under 35 U.S.C. §371 of PCT/JP95/02600, filed Feb. 18, 1995.

TECHNICAL FIELD

The present invention relates to novel heterocyclic aromatic oxazole compounds. More particularly, the present invention relates to heterocyclic aromatic oxazole compounds having antipyretic activity, analgesic activity, anti-inflammatory activity, and in particular, selective inhibitory activity against cyclooxygenase-2 (COX-2), pharmaceutically acceptable salts thereof, intermediates for producing them and pharmaceuticals useful as anti-inflammatory agents causing less side-effects such as disorders in the digestive tract, which comprise these heterocyclic aromatic oxazole compounds.

BACKGROUND ART

It has been conventionally known that arachidonic acid metabolites, prostaglandin $E_2$ ($PGE_2$), prostaglandin $I_2$ ($PGI_2$) and thromboxane $B_2$ ($TXB_2$) are deeply involved in inflammations. An important enzyme in this arachidonic acid metabolism is cyclooxygenase. Cyclooxygenase is a synthase which produces prostaglandin $H_2$ ($PGH_2$) from arachidonic acid via prostaglandin $G_2$ ($PGG_2$), and includes cyclooxygenase-1 (COX-1) and cyclooxygenase-2 (COX-2).

With respect to COX-1, cDNA cloning was performed in 1988 and its primary structure and induction by various factors have been clarified [Yokoyama, C. et al.: Biochem. Biophys. Res. Commun., 165: 888–894 (1989); Smith, W. L. et al.: Biochim. Biophys. Acta, 1083: 1–17 (1991); DeWitt, D. L.: Biochim. Biophys. Acta, 1083: 121–134 (1991)]. On the other hand, the existence of an isozyme of COX-1, namely, COX-2, was suggested in 1989 [Holtzman, M. J. et al.: J. Biol. Chem., 267: 21438–21445 (1992)], and cDNAs of COX-2 of chicken, mouse and human have been cloned since 1991 [Xie, W. et al.: Proc. Natl. Acad. Sci. USA, 88: 2692–2696 (1991); Kujubu, D. A. et al.: J. Biol. Chem., 266: 12866–12872 (1991); Hla, T. et al.: Pror. Natl. Acad. Sci. USA, 89: 7384–7388 (1992)]. COX-2 is quickly induced by phorbol ester, lipopolysacharide (LPS) and the like, and the relationship with inflammation and bronchial asthma has been inferred.

COX-1 systemically and constantly exists in almost all cells and is physiologically concerned with the generation of prostaglandin (PG) necessary for the functions of, for example, stomach and kidney. Therefore, when COX-1 is inhibited, the biosynthesis of PG by vasodilative $PGE_2$ and $PGI_2$, which protect gastric mucosa, is suppressed, and the protective action on the gastric mucosa becomes degraded, as a result of which ulcer is caused. With regard to a symptom associated with a decrease in renal blood flow, in general terms, the renal blood flow can be increased by promoting the production of vasodilative $PGE_2$ in the body, thereby to appropriately maintain glomerular filtration rate. However, if the production of such vasodilative PG is suppressed due to the inhibition of COX-1, the renal blood flow becomes less, so that a side-effect such as the onset of ischemic acute renal insufficiency is sometimes caused.

On the other hand, COX-2 exists in particular sites such as monocytes, synovial cells, granulosa cells and intravenous endothelial cells, and is topically expressed when inflammation is caused. It is therefore considered that PG generated by COX-2 is deeply concerned with inflammation and tissue disorders.

Currently, non-steroidal anti-inflammatory drugs (NSAID) such as aspirin, mefenamic acid, diclofenac, indomethacin, ibuprofen and naproxen have been widely used in clinical situations. Most of these NSAIDs are anti-inflammatory drugs which selectively inhibit cyclooxygenase (COX) and are associated with side-effects such as disorders in the digestive tract. Such side-effects are considered to be caused by the fact that they, though certainly selectively inhibit COX, inhibit both COX-1 and COX-2.

It follows therefrom that selective inhibition, without inhibition of COX-1, of solely COX-2 which is specifically induced at the inflammatory sites, would enable provision of a superior anti-inflammatory drug free of side-effects such as disorders in the digestive tract (e.g., ulcer).

There are various reports on anti-inflammatory drugs having selective COX-2 inhibitory activity, which aim at reducing side-effects such as disorders in the digestive tract.

For example, WO94/15932 discloses, as COX-2 inhibitors, 5-membered heterocyclic compounds substituted by bisaryl, such as thiophene, furan and pyrrole, which are specifically exemplified by 3-(4-methylsulfonylphenyl)-4-(4-fluorophenyl)thiophene. However, this publication merely shows a 5-membered heterocyclic compound such as thiophene having aryl or heteroaryl at the 3-position or 4-position.

Moreover, various reports deal with anti-inflammatory drugs having cyclooxygenase-inhibitory action, prostaglandin synthesis-inhibitory action or thromboxane $A_2$ synthesis-inhibitory action.

For example, Japanese Patent Unexamined Publication No. 141261/1991 discloses pyrazole derivatives such as ethyl 1-(4-fluorophenyl)-5-[4-(methylsulfonyl)phenyl]pyrazole-3carboxylate; Japanese Patent Unexamined Publication No. 183767/1982 discloses thiazole derivatives such as 2-methylthio-5-phenyl-4-(3-pyridyl)-thiazole; and Japanese Patent Unexamined Publication No. 58981/1985 discloses thiazole derivatives such as 2-ethyl-4-(4-methoxyphenyl)-5-(3-pyridyl)-1,3-thiazole. These publications mention that they are useful as anti-inflammatory drugs, whereas they do not disclose if they have selective inhibitory action on COX-2 to reduce side-effects, or any suggestion of it.

There are other reports on the following heterocyclic aromatic compounds.

For example, U.S. Pat. No. 4,632,930 discloses oxazole compounds such as 5-cyclohexyl-4-(4-methylsulfonylphenyl)-α,α-bis(trifluoromethyl)oxazole-2-methanol. Yet, the compounds disclosed therein are effective for hypertension and their use as anti-inflammatory drugs or any suggestion to that effect are not included.

Japanese Patent Application under PCT laid-open under Kohyo No. 500054/1984 discloses oxazole derivatives having heteroaryl or carbon ring aryl at the 4-position or 5-position of oxazole ring and having carboxy, ester or amidized carboxy via lower alkylene at the 2-position thereof, such as ethyl 2-[4-phenyl-5-(3-pyridyl)-oxazol-2-yl]-propionate; and Japanese Patent Application under PCT laid-open under Kohyo No. 500055/1984 discloses imidazole derivatives having heteroaryl and/or carbon ring aryl at the 4-position or 5-position of imidazole ring and having formyl or acetalized formyl via lower alkylene at the 2-position thereof, such as 2-[4-phenyl-5-(3-pyridyl)-imidazol-2-yl]-acetaldehyde dimethyl acetal. These publications teach that these compounds are effective as dermal antiphlogistic or mucosal antiphlogistic for inflammatory dermal diseases, but do not teach or even suggest that they have selective inhibitory action on COX-2.

Japanese Patent Unexamined Publication No. 70446/1993 discloses N-thiazolylsulfonamide derivatives such as N-[5-cyclohexyl-4-(4-methoxyphenyl)thiazol-2-yl] trifluoromethanesulfonamide; and Japanese Patent Unexamined Publication No. 83372/1990 discloses cyclohexylimidazole derivatives such as 4-cyclohexyl-5-phenyl-2-t-butyl-imidazole. These publications only exemplify cyclohexyl as a substituent and include no suggestion as to the substitution with phenyl substituted by aminosulfonyl, lower alkylaminosulfonyl or lower alkylsulfonyl.

WO94/27980 discloses oxazole compounds such as 2-phenyl-4-cyclohexyl-5-(4-methylsulfonylphenyl)oxazole as COX-2 inhibitors. However, the compounds described in this publication are mainly characterized by 4-fluorophenyl and 4-methylsulfonylphenyl at the 4-position and 5-position of oxazole ring, and do not suggest the compounds having specific substituents in combination, as in the present invention.

Not only in COX-2 inhibitors but also in the field of anti-inflammatory drugs, preferable phenyl substituent for 5membered heterocyclic ring skeleton has been conventionally considered to be monosubstituted phenyl such as 4-methylsulfonylphenyl and 4-methoxyphenyl, and di-substituted phenyl has been barely tried (e.g., UK Patent No. 1206403).

DISCLOSURE OF THE INVENTION

The present inventors have intensively studied with the aim of providing a novel compound having antipyretic activity, analgesic activity and anti-inflammatory activity, which is free of side-effects such as disorders in the digestive tract. Surprisingly, they have found that a compound having a secondary substituent such as halogen atom, in particular, fluorine atom, introduced into phenyl such as 4-lower allylsulfonylphenyl, 4-aminosulfonylphenyl or 4-lower alkylaminosulfonylphenyl, as a substituent for oxazole, has superior selective inhibitory action on COX-2, which resulted in the completion of the present invention.

That is, the present invention relates to heterocyclic aromatic oxazole compounds as shown in the following (1) to (21), pharmaceutically acceptable salts thereof, intermediate compounds for producing such compounds and pharmaceutical compositions comprising such heterocyclic aromatic oxazole compound.

(1) Heterocyclic aromatic oxazole compounds of the formula (I)

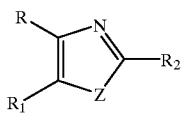

wherein

Z is an oxygen atom;

one of R and $R_1$ is a group of the formula

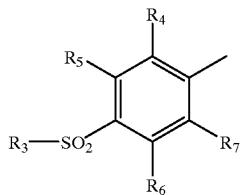

wherein $R_3$ is lower alkyl, amino or lower alkylamino, and $R_4$, $R_5$, $R_6$ and $R_7$ are the same or different and each is hydrogen atom, halogen atom, lower alkyl, lower alkoxy, trifluoromethyl, hydroxy or amino, provided that at least one of $R_4$, $R_5$, $R_6$ and $R_7$ is not hydrogen atom, and the other is optionally substituted cycloalkyl; optionally substituted heterocyclic group or optionally substituted aryl; and $R_2$ is a lower alkyl or a halogenated lower alkyl, and pharmaceutically acceptable salts thereof.

(2) Heterocyclic aromatic oxazole compounds of the above (1), wherein $R_1$ is a group of the formula

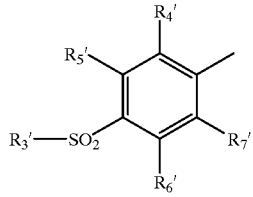

wherein $R_3'$ is lower alkyl or amino, at least one of $R_4'$, $R_5'$, $R_6'$ and $R_7'$ is halogen atom or lower alkyl and the rest is hydrogen atom or halogen atom, and pharmaceutically acceptable salts thereof.

(3) Heterocyclic aromatic oxazole compounds of the above (1), wherein $R_1$ is a group of the formula

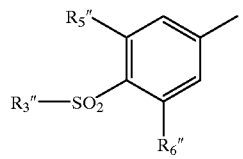

wherein $R_3''$ is methyl or amino, $R_5''$ is fluorine atom and $R_6''$ is hydrogen atom or fluorine atom, and $R_2$ is methyl, and pharmaceutically acceptable salts thereof.

(4) Heterocyclic aromatic oxazole compounds of the above (1), wherein $R_1$ is a group of the formula

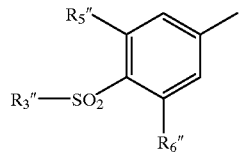

wherein $R_3^{1''}$, $R_5''$ and $R_6''$ are as defined in the above (3); R is optionally substituted cycloalkyl having 5 to 7 carbon atoms, optionally substituted thienyl, optionally substituted furyl, optionally substituted pyrrolyl, optionally substituted morpholino, optionally substituted piperazinyl, optionally substituted piperidyl, optionally substituted phenyl, optionally substituted naphthyl or optionally substituted biphenyl, and $R_2$ is methyl, and pharmaceutically acceptable salts thereof.

(5) Heterocyclic aromatic oxazole compounds of the above (4), wherein $R_3''$ is amino, and pharmaceutically acceptable salts thereof.
(6) Heterocyclic aromatic oxazole compounds of the above (4), wherein R is optionally substituted cycloalkyl having 5 to 7 carbon atoms, optionally substituted phenyl or optionally substituted thienyl, and pharmaceutically acceptable salts thereof.
(7) Heterocyclic aromatic oxazole compounds of the above (4), wherein R is cyclohexyl or 4-fluorophenyl, and $R_1$ is 4-aminosulfonyl-3-fluorophenyl, 4-aminosulfonyl-3,5-difluorophenyl, 3-fluoro-4-methylsulfonylphenyl or 3,5-difluoro-4-methylsulfonylphenyl, and pharmaceutically acceptable salts thereof.
(8) Heterocyclic aromatic oxazole compounds of the above (1), which are selected from the group of:
4-cyclohexyl-5-(3-fluoro-4-methylsulfonylphenyl)-2-methyloxazole,
5-(4-aminosulfonyl-3-fluorophenyl)-4-cyclohexyl-2-methyloxazole,
5-(4-aminosulfonyl-3,5-difluorophenyl)-4-cyclohexyl-2-methyloxazole,
4-cyclohexyl-5-(3,5-difluoro-4-methylsulfonylphenyl)-2-methyloxazole, and
5-(4-aminosulfonyl-3-fluorophenyl)-4-(4-fluorophenyl)-2-methyloxazole, and pharmaceutically acceptable salts thereof.
(9) Oxime compounds of the following formula (XI')

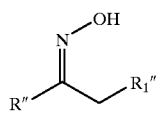

(XI')

wherein $R_1''$ is

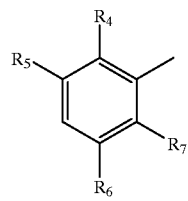

wherein $R_4$, $R_5$, $R_6$ and $R_7$ are as defined in the above (1), and $R_1''$ is optionally substituted cycloalkyl or optionally substituted aryl.
(10) Oxime compounds of the above (9) wherein $R_1''$ is 3-fluorophenyl or 3,5-difluorophenyl, and R" is cyclohexyl or 4-fluorophenyl.
(11) Ketone compounds of the following formula (IV")

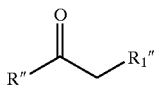

(IV")

wherein $R_1''$ and R" are respectively as defined in the above (9).
(12) Ketone compounds of the above (11) wherein $R_1''$ is 3-fluorophenyl or 3,5-difluorophenyl, and R" is cyclohexyl or 4-fluorophenyl.
(13) Ketomethylene compounds of the following formula (IV''')

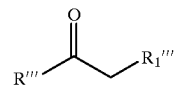

(IV''')

wherein R''' is optionally substituted cycloalkyl having 5 to 7 carbon atoms, optionally substituted phenyl or optionally substituted thienyl, and $R_1'''$ is a group of the formula

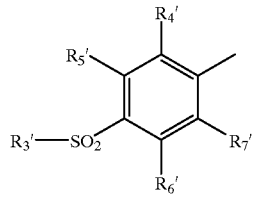

wherein $R_3'$, $R_4'$, $R_5'$, $R_6'$ and $R_7'$ are as defined in the above (2).
(14) Ketomethylene compounds of the above (13) wherein R''' is cyclohexyl, and $R_1'''$ is 4-aminosulfonyl-3-fluorophenyl, 4-aminosulfonyl-3,5-difluorophenyl, 3-fluoro-4-methylsulfonylphenyl or 3,5-difluoro-4-methylsulfonylphenyl.
(15) Ester compounds of the following formula (V)

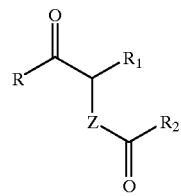

(V)

wherein R, $R_1$, $R_2$ and Z are as defined in the above (1).
(16) Ester compounds of the above (15) wherein R is cycloalkyl and $R_2$ is lower alkyl.
(17) Amide compounds of the following formula (XVIII')

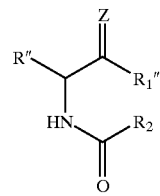

(XVIII')

wherein $R_1''$ and R" are respectively as defined in the above (9), and Z and $R_2$ are as defined in the above (1).
(18) Amide compounds of the above (17) wherein $R_1''$ is 3-fluorophenyl or 3,5-difluorophenyl, R" is cyclohexyl or 4-fluorophenyl, and $R_2$ is lower alkyl.
(19) Pharmaceutical compositions comprising a pharmaceutically acceptable carrier, and a heterocyclic aromatic oxazole compound of the above (1) or a pharmaceutically acceptable salt thereof.
(20) Cyclooxygenase-2 inhibitors comprising a pharmaceutically acceptable carrier, and a heterocyclic aromatic oxazole compound of the above (1) or a pharmaceutically acceptable salt thereof as an active ingredient.

(21) Anti-inflammatory agents comprising a pharmaceutically acceptable carrier, and a heterocyclic aromatic oxazole compound of the above (1) or a pharmaceutically acceptable salt thereof as an active ingredient.

As used herein, lower alkyl means an optionally branched alkyl having 1 to 4 carbon atoms, which is exemplified by methyl, ethyl, propyl, isopropyl, butyl, isobutyl, sec-butyl and tert-butyl, with preference given to methyl.

Lower alkylamino is that wherein amino group is substituted by the above-mentioned lower alkyl, and is exemplified by methylamino, dimethylamino, ethylamino, diethylamino, propylamino, isopropylamino, butylamino, isobutylamino, sec-butylamino and tert-butylamino. Preferred are methylamino and dimethylamino.

Halogen atom means chlorine atom, bromine atom, fluorine atom and the like, with preference given to chlorine atom and fluorine atom. Particularly preferred is fluorine atom.

Lower alkoxy is an optionally branched alkoxy having 1 to 4 carbon atoms, which is exemplified by methoxy, ethoxy, propoxy, isopropoxy, butoxy, isobutoxy, sec-butoxy and tert-butoxy, with preference given to methoxy.

Cycloalkyl means a cycloalkyl having 3 to 8 carbon atoms, which is exemplified by cyclopropyl, cyclobutyl, cyclopentyl, cyclohexyl, cycloheptyl and cyclooctyl, with preference given to cycloalkyl having 5 to 7 carbon atoms, such as cyclopentyl, cyclohexyl and cycloheptyl. Particularly preferred is cyclohexyl.

Heterocyclic group is a 5- or 6-membered aromatic heterocyclic ring, saturated heterocyclic ring or condensed heterocyclic ring of these heterocyclic rings and benzene ring, all having, besides carbon atom, 1 to 3 hetero atoms selected from nitrogen atom, oxygen atom and sulfur atom as atom(s) constituting the ring. Examples thereof include thienyl, furyl, pyrrolyl, imidazolyl, pyrazolyl, thiazolyl, isothiazolyl, oxazolyl, isoxazolyl, morpholino, piperazinyl, piperidyl, pyranyl, thiopyranyl, pyridyl, benzothienyl, benzofuranyl, indole, 4,5,6,7-tetrahydroindole, 4,5,6,7-tetrahydrobenzothienyl and 4,5,6,7-tetrahydrobenzofuranyl, with preference given to thienyl, furyl, pyrrolyl, morpholino, piperazinyl and piperidyl, and particular preference given to thienyl.

Aryl is, for example, phenyl, naphthyl or biphenyl. Preferred is phenyl.

Halogenated lower alkyl is that wherein lower alkyl is substituted by the aboventioned halogen atom, and is exemplified by fluoromethyl, chloromethyl, bromomethyl, iodomethyl, difluoromethyl, dichloromethyl, trifluoromethyl, trichloromethyl, fluoroethyl, chloroethyl, difluoroethyl, dichloroethyl, trifluoroethyl, trichloroethyl, tetrachloroethyl, pentafluoroethyl and fluoropropoyl, with preference given to fluoromethyl, chloromethyl, dichlpromethyl, difluoromethyl, trichloromethyl and trifluoromethyl.

"Optionally substituted" means that the group may be substituted by 1 to 3 substituents wherein said substituents may be the same or different. The position of the substituents is optional and is not particularly limited. Specific examples include lower alkyl such as methyl, ethyl, propyl, isopropyl, butyl and tert-butyl; hydroxy; lower alkoxy such as methoxy, ethoxy, propoxy and butoxy; halogen atom such as fluorine, chlorine and bromine; nitro; cyano; acyl such as formyl, acetyl and propionyl; acyloxy such as formyloxy, acetyloxy and propionyloxy; mercapto; alkylthio such as methylthio, ethylthio, propylthio, butylthio and isobutylthio; amino; alkylamino such as methylamino, ethylamino, propylamino and butylamino; dialkylamino such as dimethylamino, diethylamino, dipropylamino and dibutylamino; carbonyl; alkoxycarbonyl such as methoxycarbonyl, ethoxycarbonyl and propoxycarbonyl; amide; trifluoromethyl; alkylsulfonyl such as methylsulfonyl and ethanesulfonyl; aminosulfonyl; cycloalkyl such as cyclopentyl and cyclohexyl; phenyl; and acylamide such as acetamide and propionylamide. Preferred are hydroxy, lower alkyl, lower alkoxy, mercapto, lower alkylthio, halogen atom, trifluoromethyl, alkylcarbonyl, alkoxycarbonyl and acylamide.

More specifically, optionally substituted aryl means an aryl which may be substituted by halogen atom, hydroxy, lower alkyl, lower alkoxy, lower alkylsulfonyl and aminosulfonyl, particularly phenyl, and is exemplified by phenyl, fluorophenyl, methylphenyl, methoxyphenyl, methylsulfonylphenyl and aminosulfonylphenyl, with preference given to phenyl and 4-fluorophenyl.

Optionally substituted heterocyclic group means a heterocyclic group which may be substituted by halogen atom, hydroxy, lower alkyl, lower alkoxy, lower alkylsulfonyl and aminosulfonyl, and particularly means thienyl, furyl, 5-methylthienyl and 5-chlorothienyl. Optionally substituted cycloalkyl means a cycloalkyl which may be substituted by the same substituents as above, with preference given to cyclohexyl.

Examples of preferable R of the heterocyclic aromatic oxazole compounds of the present invention include cyclohexyl, 4-fluorophenyl and 5-chlorothienyl, with particular preference given to cyclohexyl. Preferred as $R_1$ is a group of the formula

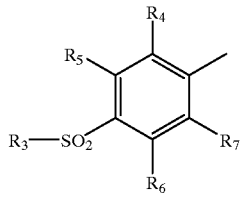

wherein $R_3$, $R_4$, $R_5$, $R_6$ and $R_7$ are as defined above, with particular preference given to a group wherein $R_3$ is amino or methyl, $R_4$ and $R_7$ are hydrogen atoms and at least one of $R_5$ and $R_6$ is fluorine atom. Specific examples include 4-aminosulfonyl-3-fluorophenyl, 3-fluoro-4-methylsulfonylphenyl, 4-aminosulfonyl-3,5-difluorophenyl and 3,5-difluoro-4-methylsulfonylphenyl, with particular preference given to 4-aminosulfonyl-3-fluorophenyl. Preferred as $R_2$ is methyl.

Pharmaceutically acceptable salt may be any as long as it forms a non-toxic salt with the oxazole derivative of the formula (I). Alkali metal salts such as sodium salt and potassium salt, alkaline earth metal salts such as magnesium salt and calcium salt, ammonium salt, organic base salts such as trimethylamine salt, triethylamine salt, pyridine salt, picoline salt, dicyclohexylamine salt and N,N'-dibenzylethylenediamine salt, and amino acid salts such as lysine salt and arginine salt are among the examples. It may be a hydrate as the case demands.

The compound of the present invention has particularly superior selective inhibitory action on COX-2 and is expected to make a therapeutic drug useful for antipyresis, pain relief and anti-inflammation, which is free of side-effects such as digestive tract disorders.

When the compound of the formula (I) of the present invention or a pharmaceutically acceptable salt thereof is used as a pharmaceutical preparation, it is generally admixed with pharmacologically acceptable carriers, excipients, diluents, extenders, disintegrators, stabilizers, preservatives, buffers, emulsifying agents, aromatics, colorings, sweeteners, thickeners, flavorings, solubilizers and other additives known per se, such as water, vegetable oil, alcohol such as ethanol and benzyl alcohol, polyethylene glycol, glycerol triacetate gelatin, carbohydrates such as lactose and starch, magnesium stearate, talc, lanolin and petrolatum, and formulated into, by a conventional method, tablets, pills, powders, granules, suppositories, injections, eye drops, liquids, capsules, troches, aerosols, elixirs, suspensions, emulsions, syrups and the like, which can be administered orally or parenterally.

While the dose varies depending on the kind and severity of the disease,, compound to be administered, administration route, and age, sex, body weight etc. of patients, 0.1 mg–1,000 mg, particularly 1 mg–300 mg of compound (I) is generally administered orally to an adult per day.

The compounds of the present invention can be produced, for example, by the following methods. It is needless to say that the method for producing the compounds of the present invention is not limited to these methods.

Step 2

Compound (V) can be synthesized by reacting compound (IV) in acetic acid solvent in the presence of lead tetraacetate, or by refluxing compound (IV) under heating in the presence of a complex such as manganese acetate, in lower alkanecarboxylic acid such as acetic acid and propionic acid corresponding to $R_2COOH$ wherein $R_2$ is as defined above and benzoic acid and a solvent such as benzene as necessary.

Step 3

Compound (I) can be synthesized by refluxing compound (V) under heating in the presence of ammonium salt (e.g., lower alkanecarboxylic acid ammonium such as ammonium acetate and ammonium formate), and inorganic ammonium such as ammonium carbonate in an acidic solvent such as lower alkanecarboxylic acid (e.g., formic acid, acetic acid and propionic acid). In this reaction, when R or $R_1$ is aromatic heterocycle, isomers may be produced wherein the 4-position R and the 5-position $R_1$ are reversed.

Compound (I) can be also synthesized by the following route.

Step 4 wherein $X_1$ is hydroxy

This step, Step 6 and Step 7 are advantageous when $R_2$ (e.g., methyl) is converted to other $R_2$ (e.g., $R_2'$ such as ethyl).

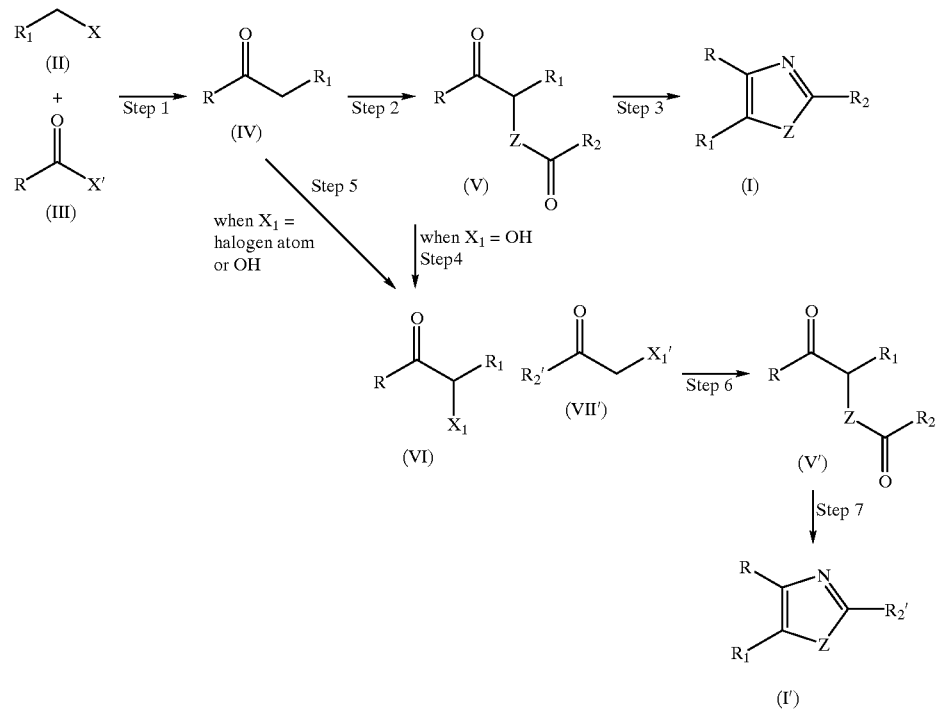

wherein $R_2'$ is lower alkyl or halogenated lower alkyl wherein $R_2'$ may be the same with or different from $R_2$, X and X' are the same or different and each is halogen atom such as bromine atom and chlorine atom, $X_1$ is halogen atom or hydroxy, $X_1'$ is halogen atom or hydroxy or alkali metal derivative thereof, and R, $R_1$, $R_2$ and Z are as defined above.

Step 1

Compound (IV) can be synthesized by reacting compound (II) with compound (III) in the presence of a metal such as zinc and magnesium in an inert solvent such as 1,2-dimethoxyethane, dioxane, ether, tetrahydrofuran, methylene chloride, benzene and toluene at room temperature. In this case, a catalyst such as palladium(O) complex and copper(I) complex may be added.

When $X_1$ is hydroxy, compound (VI) can be synthesized by reacting compound (V) in the presence of a base such as potassium carbonate, lithium hydroxide, sodium hydroxide and potassium hydroxide in an organic solvent such as methanol, ethanol and dioxane, water or a mixed solvent thereof from under cooling to under heating.

Compound (VI) can be also synthesized by the following Step 5.

Step 5 wherein $X_1$ is halogen atom or hydroxy

Compound (VI) can be synthesized by reacting compound (IV) in the presence of a halogenating agent such as bromine, chlorine and N-bromosuccinimide in an inert solvent such as acetic acid, 1,2-dimethoxyethane, dioxane, ether, tetrahydrofuran, methylene chloride, benzene and toluene to give compound (VI) wherein $X_1$ is halogen atom.

Compound (VI) wherein $X_1$ is hydroxy can be synthesized by oxidizing compound (IV) with an oxidizing agent such as benzene iodoacetate, or by treating the halogenated compound (VI) obtained above with water in an inert solvent such as acetone, 1,2-dimethoxyethane, dioxane, ether, tetrahydrofuran, benzene and toluene.

Step 6

Compound (V') can be obtained by reacting compound (VI) and compound (VII') by a known method. Specifically, compound (VI) wherein $X_1$ is hydroxy and compound (VII') wherein $X_1'$ is halogen atom, or compound (VI) wherein $X_1$ is halogen atom and compound (VII') wherein $X_1'$ is hydroxy are reacted in pyridine, or in the presence of a base such as triethylamine and sodium hydroxide, in an organic solvent such as methylene chloride, chloroform and ethanol, from under cooling to under heating. When $X_1$ is halogen atom, alkali metal salt such as sodium acetate may be used instead of carboxylic acid compound (VII'). In this case, a base may or may not be added.

Step 7

Compound (I') can be obtained by treating compound (V') in the same manner as in Step 3.

When a compound wherein either R or $R_1$ is 4-aminosulfonyl-3-fluorophenyl is desired, the compound can be produced from a compound having 3-fluoro-4-methylsulfonylphenyl corresponding to the objective compound by a known method.

Instead of obtaining compound (IV) using, as mentioned above, compound (II) or (III) having, as R or $R_1$,

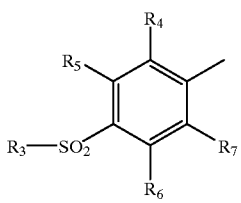

wherein $R_3$, $R_4$, $R_5$, $R_6$ and $R_7$ are as defined above, compound (II') or (III') having

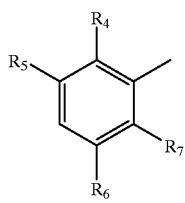

wherein $R_4$, $R_5$, $R_6$ and $R_7$ are as defined above, may be used as a starting material to give compound (IV') according to Step 10, which compound is then converted to aminosulfonyl or methylsulfonyl according to the method of Step 15 to give compound (IV). Alternatively, such starting materials (II') and (III') may be used to give a non-sulfonylated oxazole compound (XIII) corresponding to the ultimate compound (I) or (I') according to Step 1 to Step 7, and the obtained compound (XIII) may be subjected to sulfonylation in the same manner as in Step 15 to give the objective compound (I) or (I').

When a compound wherein either R or $R_1$ is phenyl substituted by alkylaminosulfonyl or aminosulfonyl is desired, compound (X) wherein either $R_8$ or $R_9$ is methoxysulfonylphenyl is subjected to the following Step 8 and Step 9 to synthesize compound (IV).

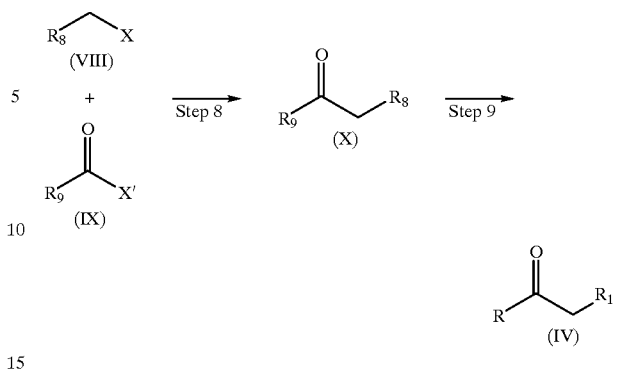

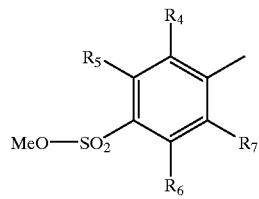

wherein either $R_8$ or $R_9$ is methoxysulfonylphenyl of the formula wherein $R_4$, $R_5$, $R_6$ and $R_7$ are as defined above, and the other is optionally substituted cycloalkyl, optionally substituted heterocyclic group or optionally substituted aryl, and R, $R_1$, X and X' are as defined above.

Step 8

Compound (X) can be synthesized in the same manner as in Step 1, using compound (VIII) and compound (IX).

Step 9

When at least one of R and $R_1$ is phenyl having aminosulfonyl or alkylsulfonyl at the 4-position, compound (IV) can be synthesized by heating compound (X) in pyridine, or refluxing compound (X) under heating in the presence of sodium iodide, potassium iodide, lithium iodide and the like, in an organic solvent such as acetone and tetrahydrofuran, after which the obtained compound is reacted with thionyl chloride or oxalyl chloride under heating. Then, the resulting product is aminated or alkylaminated or alkylated by a known method. More specifically, amination or alkylamination is carried out by reacting the resulting product in the presence of aqueous ammonia or alkylamine, or a base such as sodium acetate and ammonium salt such as alkylamine hydrochloride, in an organic solvent such as tetrahydrofuran, ether, toluene, benzene, methylene chloride and dioxane from under cooling to under heating. The alkylation can be carried out by the method described in J. Org. Chem., 56: 4974–4976 (1991).

Compound (I) can be also synthesized by the method of the following Step 10 to Step 15.

This method is directed to finally introducing sulfonyl group in the last Step 15.

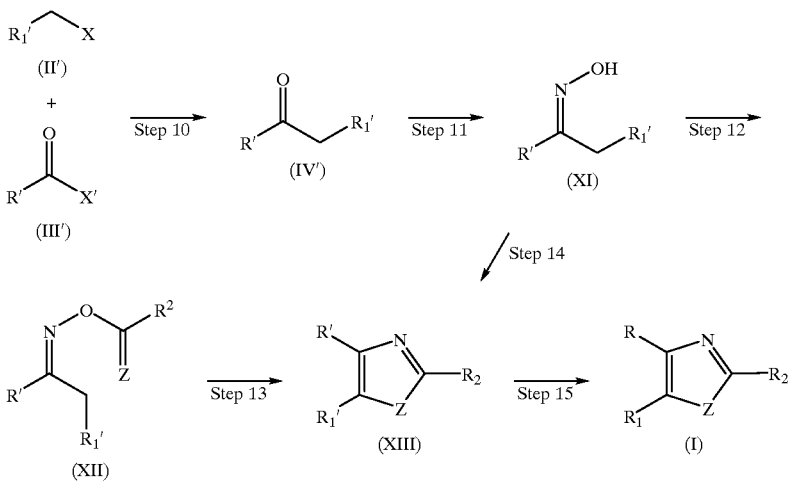

wherein either R' or $R_1'$ is phenyl of the formula

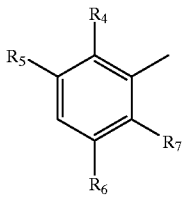

wherein $R_4$, $R_5$, $R_6$ and $R_7$ are as defined above, and the other is a group corresponding to one of R and $R_1$, cycloalkyl which may be substituted by a substituent such as lower alkyl, heterocyclic group such as thienyl and furyl, which may be substituted by a substituent lower alkyl or halogen atom, or aryl which may be substituted by a substituent such as halogen atom, lower alkyl and lower alkoxy, and R, $R_1$, X, X' and Z are as defined above.

Step 10

Compound (IV') can be synthesized in the same manner as in Step 1, wherein compound (II') and compound (III') are reacted in the presence of a metal such as zinc and magnesium in an inert solvent such as 1,2-dimethoxyethane, dioxane, ether, tetrahydrofuran, methylene chloride, benzene and toluene at room temperature. In this case, a catalyst such as palladium(O) complex and copper(I) iodide complex may be added.

Step 11

Compound (XI) can be synthesized by refluxing under heating compound (IV') and hydroxylammine hydrochloride in the presence of a base such as sodium acetate, sodium hydroxide and potassium carbonate in an organic solvent such as methanol, ethanol and tetrahydrofuran, water or a mixed solvent thereof.

Step 12

Compound (XII) can be synthesized by reacting compound (XI) in the presence of an acylating agent such as acetic anhydride and acetyl chloride, in pyridine, or in the presence of a base such as triethylamine in an organic solvent such as methylene chloride and chloroform from under cooling to under heating.

Step 13

Compound (XIII) can be synthesized by refluxing under heating compound (XII) in an acidic solvent such as formic acid and acetic acid. In this case, a dehydrating agent such as magnesium sulfate and sodium sulfate may be added.

Step 14

This step is for the synthesis of compound (XIII) from compound (XI) in a single step, and o und (XIII) can be synthesized from compound (XI) and carboxylic acid chloride such as acetyl chloride by the method described in Indian J. Chem., 20B: 322–323 (1981). When $R_2$ is methyl, compound (XIII) can be synthesized by reacting compound (XI) and acetic anhydride while heating in acetic acid.

Step 15

Compound (I) can be synthesized by reacting compound (XIII) in the presence of a chlorosulfonylating agent such as chlorosulfonic acid in an organic solvent such as chloroform and methylene chloride, or without solvent, and subjecting the resulting product to amination, alkylamination or alkylation by a known method. The amination and alkylamination in Step 15 specifically comprise reacting in the presence of aqueous ammonia, alkylamine or a base such as sodium acetate and ammonium salt such as alkylamine hydrochloride in an organic solvent such as tetrahydrofuran, ether, toluene, benzene, methylene chloride and dioxane from under cooling to under heating. When alkylsulfonation is carried out, the method described in J. Org. Chem., 56: 4974–4976 (1991) can be used for the synthesis.

In the above description, alkylsulfonation or aminosulfonation in the final Step 15 has been exemplary discussed. It is possible to use compound (II) and compound (III) instead of the starting materials (II') and (III') to give compound (IV), which is followed by Step 11 to Step 14 to give an oxazole compound (I). In this case, Step 15 is not necessary.

Compound (XIII) used in Step 15 can be also synthesized by the following route.

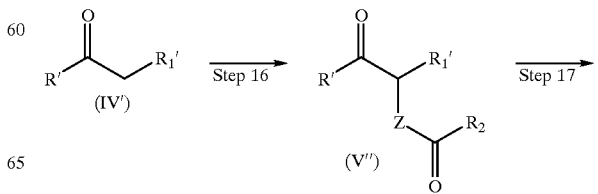

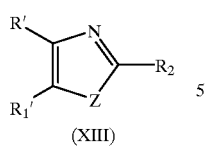

wherein R', $R_1'$, $R_2$ and Z are as defined above.

Step 16

Compound (VI') can be synthesized in the same manner as in Step 2 wherein compound (IV') is reacted in the presence of lead tetraacetate in acetic acid solvent, or by heating compound (IV') in the presence of a complex such as manganese acetate in lower akanecarboxylic acid such as acetic acid and propionic acid corresponding to $R_2COOH$ wherein $R_2$ is as defined above, and benzoic acid and in a solvent such as benzene as necessary.

Step 17

Compound (XIII) can be synthesized in the same manner as in Step 3 wherein compound (V") is refluxed under heating in the presence of ammonium salt such as lower alkanecarboxylic acid ammonium (e.g., ammonium acetate and ammonium formate) and inorganic ammonium (e.g., ammonium carbonate) in an acidic solvent of lower alkanecarboxylic acid such as formic acid, acetic acid and propionic acid. In this reaction, when R' or $R_1'$ is an aromatic heterocycle, isomers may be produced wherein the 4-position R' and the 5-position $R_1'$ are reversed.

Compound (I) can be also synthesized by the method shown in the following Step 18 to Step 21.

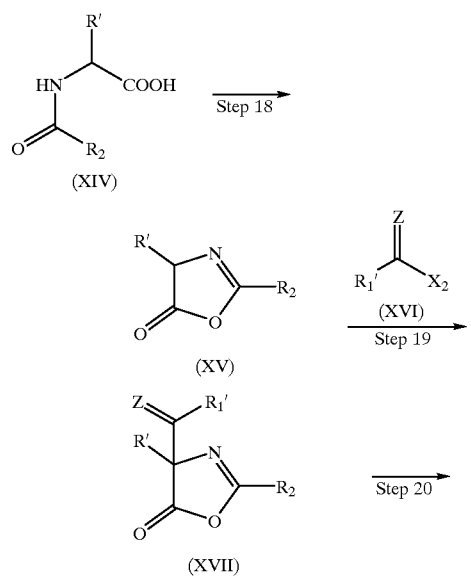

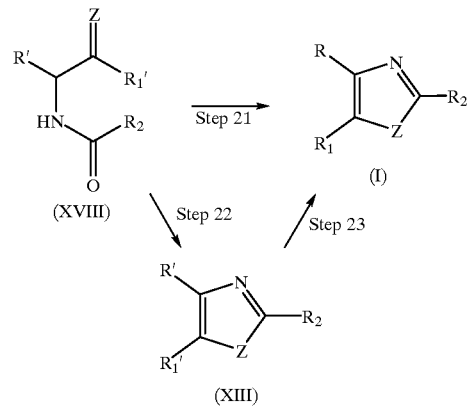

wherein $X_2$ is halogen atom, and R, $R_1$, R', $R_1'$, $R_2$ and Z are as defined above.

Step 18

Compound (XV) can be synthesized by reacting compound (XIV) with chlorbonate such as ethyl chlorocaronate in an inert solvent such as tetrahydrofuran, toluene and ethyl acetate in the presence of a base such as triethylamine, or by heating compound (XIV) in acetic anhydride.

Step 19

Compound (XVII) can be synthesized by reacting compound (XV) with compound (XVI) or an acid anhydride corresponding to compound (XVI) in an inert solvent such as tetrahydrofuran, acetonitrile, ethyl acetate and toluene in the presence of magnesium salt such as magnesium chloride and a base such as triethylamine, pyridine and potassium carbonate. Compound (XVII) can be also synthesized by the method described in Chem. Ber., 102: 883–898 (1969).

Step 20

Compound (XVIII) can be synthesized by treating compound (XVII) with an acid such as 1N-4N hydrochloric acid, oxalic solid and dilute sulfuric acid in an inert solvent such as tetrahydrofuran, dioxane, methylene chloride and toluene, or heating compound (XVII) in the presence of pyridine and acetic acid.

Step 21

Compound (I) is obtained by reacting compound (XVIII) with a chlorosulfonylating agent such as chlorosulfonic acid in an organic solvent such as chloroform and methylene chloride, or without solvent. Then, the obtained product is reacted with aqueous ammonia or alkylamine in an orgnic solvent such as tetrahydrofuran, ether, toluene, methylene chloride and dioxane, or reacted with ammonium salt such as alkylamine hydrochloride in the presence of a base such as sodium acetate, pyridine and sodium hydroxide.

Compound (I) can be also synthesized from compound (XVIII) by the following Step 22 and Step 23.

Step 22

Compound (XIII) can be synthesized by reacting compound (XVIII) with inorganic acid such as concentrated sulfuric acid and polyphosphoric acid in acetic anhydride, or without solvent, at room temperature to under heating.

Step 23

Compound (I) can be synthesized by reacting compound (XIII) in the same manner as in the aforementioned. Step 15.

In the above Step 22 and Step 23, alkylsulfonylation or aminosulfonylation in the final Step 23 has been exemplary discussed. It is possible to subject a compound having R and $R_1$ instead of R' and $R_1'$ to the reaction according to Step 18 to Step 20, followed by Step 22 to give an oxazole compound (I). In this case, Step 23 is not necessary.

The compound (I) thus obtained can be isolated and purified by a known method for separation and purification, such as concentration, concentration under reduced pressure, solvent extraction, crystal precipitation, recrystallization and chromatography.

The present invention is described in more detail in the following by illustrative Examples and Experimental Examples, to which the present invention is not limited.

EXAMPLE 1

Synthesis of 5-(2-chloro-4-methylsulfonylphenyl)-4-cyclohexyl-2-methyloxazole (formula (I'); R=cyclohexyl, $R_1$=2-chloro-4-methylsulfonylphenyl, $R_2'$=methyl, Z=oxygen atom)

Step 1) 2-Chloro-4-methylsulfonylbenzyl cyclohexyl ketone (formula (IV); R=cyclohexyl, $R_1$=2-chloro-4-methylsulfonylphenyl)

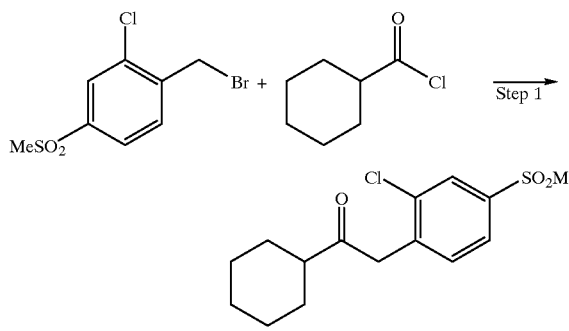

To a solution of tetrakis(triphenylphosphine)palladium (1.29 g) and zinc powder (2.19 g) in 1,2-dimethoxyethane (10 ml) was added a solution of cyclohexanecarbonyl chloride (3.60 g) in 1,2-dimethoxyethane (10 ml) at room temperature under a nitrogen atmosphere. A solution of 2-chloro-4methylsulfonylbenzyl bromide (9.40 g) in 1,2-dimethoxyethane (20 ml) was gradually added dropwise to the mixture at room temperature with stirring. The mixture was further stirred at room temperature for 3 hours. The insoluble matter was removed by filtration and the filtrate was concentrated under reduced pressure. Then, ethyl acetate (200 ml) was added to the residue, and the mixture was washed with 1N hydrochloric acid, and then with saturated aqueous sodium hydrogencaitonate solution and saturated brine, and dried over anhydrous sodium sulfate. The solvent was evaporated, and ethyl acetate and diisopropyl ether were added. The precipitated solid was collected by filtration to give 3.47 g of the title compound as a white solid.

Step 5) 2-Bromo-2-(2-chloro-4-methylsulfonylphenyl)-1-cyclohexyl-1-ethanone (formula (VI); R=cyclohexyl, $R_1$=2-chloro-4-methylsulfonylphenyl, $X_1$=bromine atom)

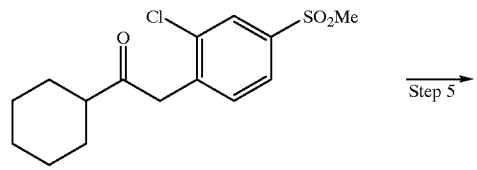

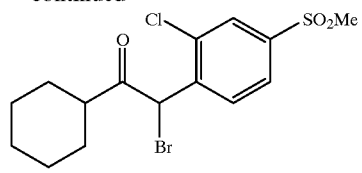

To a solution of the compound (3.40 g) obtained in the above Step 1) in benzene (20 ml) was dropwise added a solution of bromine (1.73 g) in benzene (20 ml) with stirring under ice-cooling, and the mixture was stirred for one hour. This solution was poured into water and extracted with ethyl acetate. The organic layer was washed with saturated aqueous sodium hydrogencarbonate solution and saturated brine, and dried over anhydrous sodium sulfate. The solvent was evaporated under reduced pressure to give 4.20 g of the title compound.

Step 6) 1-(2-Chloro-4-methylsulfonylphenyl)-2-cyclohexyl-2-oxoethyl acetate (formula (V'); R=cyclohexyl, $R_1$=2-chloro-4-methylsulfonylphenyl, $R_2'$=methyl, Z=oxygen atom)

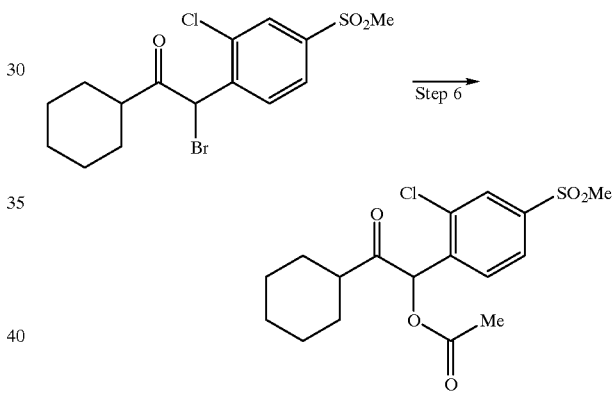

Sodium acetate (1.06 g) and ethanol (40 ml) were added to the compound (4.20 g) obtained in the above Step 5) The mixture was refluxed under heating for 4 hours, and the solvent was evaporated under reduced pressure. Ethyl acetate was added to the residue. The mixture was washed with water and saturated brine, and dried over anhydrous sodium sulfate. The solvent was evaporated to give 3.85 g of a crude product of the title compound.

Step 7) 5-(2-Chloro-4-methylsulfonylphenyl)-4-cyclohexyl-2-methyloxazole (formula (I'); R=cyclohexyl, $R_1$=2-chloro-4-methylsulfonylphenyl, $R_2'$=methyl, Z=oxygen atom)

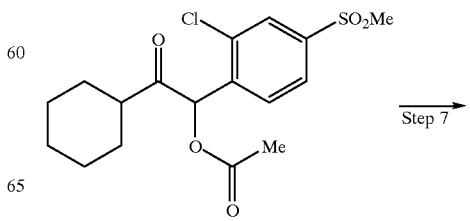

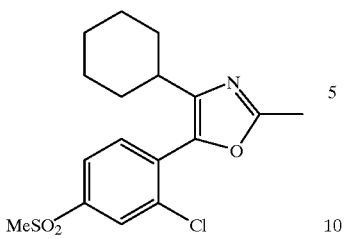

A solution of the compound (3.85 g) obtained in the above Step 6) and ammonium acetate (2.08 g) in acetic acid (40 ml) was refluxed under heating for 5 hours. The solvent was evaporated under reduced pressure, and ethyl acetate was added to the residue. The mixture was washed with water, saturated aqueous sodium hydrogencarbonate solution and saturated brine, and dried over anhydrous sodium sulfate. The solvent was evaporated under reduced pressure to give 1.95 g of the title compound (yield 53%).

EXAMPLE 2

Synthesis of 5-(4-aminosulfonyl-3-fluorophenyl)-4-cyclohexyl-2-methyloxazole (formula (I); R=cyclohexyl, $R_1$=4-aminosulfonyl-3-fluorophenyl, $R_2$=methyl, Z=oxygen atom)

Step 10) Cyclohexyl 3-fluorobenzyl ketone (formula (IV'); R'=cyclohexyl, $R_1$'=3-fluorophenyl)

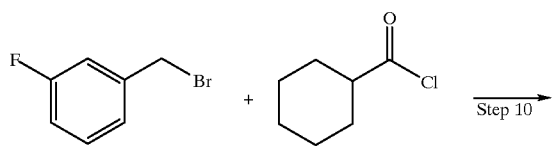

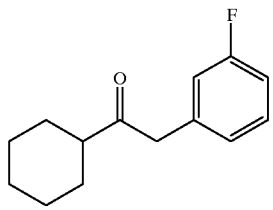

To a solution of tetrakis(triphenylphosphine)palladium (2.00 g) and zinc powder (17.98 g) in 1,2-dimethoxyethane (50 ml) was added a solution of cyclohexanecarbonyl chloride (20.00 g) in 1,2-dimethoxyethane (50 ml) at room temperature under a nitrogen atmosphere. A solution of 3-fluorobenzyl bromide (26.00 g) in 1,2-dimethoxyethane (100 ml) was gradually added dropwise to the mixture with stirring under ice-ling. The mixture was stirred under ice-cooling for 30 minutes, and at room temperature for 2 hours. The insoluble matter was removed by filtration and the filtrate was concentrated under reduced pressure. Then, ethyl acetate (200 ml) was added to the residue, and the mixture was washed with 1N hydrochloric acid, and then with saturated aqueous sodium hydrogencarbonate solution and saturated brine, and dried over anhydrous sodium sulfate. The solvent was evaporated to give 29.20 g of an oily crude product.

Step 16) 2-Cyclohexyl-1-(3-fluorophenyl)-2-oxoethyl acetate (formula (V''); R'=cyclohexyl, $R_1$'=3-fluorophenyl, $R_2$'=methyl, Z=oxygen atom)

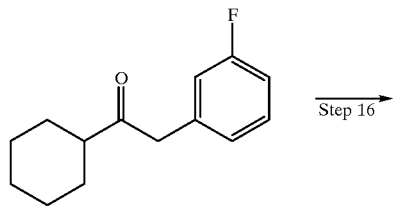

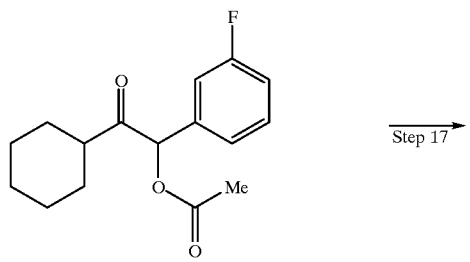

Lead tetraacetate (75.00 g) was added to a solution of the compound (29.20 g) obtained in the above Step 10) in acetic acid (300 ml). The mixture was refluxed under heating for 1.5 hours, and the solvent was evaporated under reduced pressure. Ethyl acetate was added to the residue. The mixture was washed with water, a saturated aqueous sodium hydrogencarbonate solution and saturated brine, and dried over anhydrous sodium sulfate. The solvent was evaporated under reduced pressure, and the residue was purified by silica gel column chromtography (developing solvent; hexane:ethyl acetate=9:1) to give 18.30 g of the title compound as an oil (yield 50%).

Step 17) 4-Cyclohexyl-5-(3-fluorophenyl)-2-methyloxazole (formula (XIII); R'=cyclohexyl, $R_1$'=3-fluorophenyl, $R_2$=methyl, Z=oxygen atom)

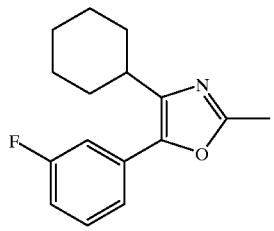

A solution of the compound (18.00 g) obtained in the above Step 16) and ammonium acetate (15.00 g) in acetic acid (100 ml) was refluxed under heating for 5 hours, and the solvent was evaporated under reduced pressure. Ethyl acetate was added to the residue. The mixture was washed with water, saturated aqueous sodium hydrogencaraonate solution and saturated brine, and dried over anhydrous sodium sulfate. The solvent was evaporated under reduced pressure to give 17.20 g of an oily crude product.

Step 15) 5-(4-Aminosulfonyl-3-fluorophenyl)-4-cyclohexyl-2methyloxazole (formula (I); R=cyclohexyl, $R_1$=4-aminosulfonyl-3-fluorophenyl, $R_2$=methyl, Z=oxygen atom)

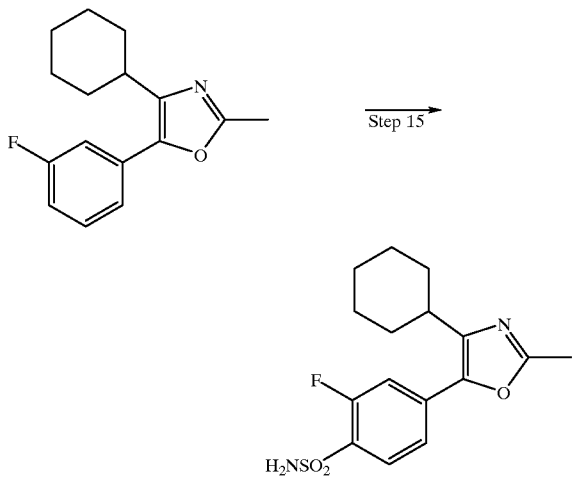

To a solution of the compound (17.00 g) obtained in the above Step 17) in chloroform (80 ml) was added dropwise chlorosulfonic acid (27 ml) with stirring under ice-cooling, and the mixture was heated at 100° C. for 3 hours. The reaction mixture was cooled to room temperature, and dropwise added to ice-water (300 ml) with stirring. The organic layer was separated, washed with saturated brine, and dried over anhydrous sodium sulfate. The solvent was evaporated under reduced pressure to give 20.31 g of a crude product.

Aqueous ammonia (28%) was added to a solution of the obtained compound (10.00 g) in tetrahydrofuran (40 ml) with stirring at room temperature, and the mixture was stirred at room temperature for one hour. The solvent was evaporated under reduced pressure and ethyl acetate was added to the residue. The mixture was washed with water and saturated brine, and dried over anhydrous sodium sulfate. The solvent was evaporated, and the residue was separated and purified by silica gel column chromatography (developing solvent; dichloromethane:ethyl acetate=6:1) to give 5.74 g of the title compound (yield 61%).

EXAMPLE 2'

The compound of Example 2 (formula (I); R=cyclohexyl, $R_1$=4-aminosulfonyl-3-fluorophenyl, $R_2$=ethyl, Z=oxygen atom) was synthesized according to another synthetic method.

Step 11) Cyclohexyl 3-fluorobenzyl ketone oxime (formula (XI); R'=cyclohexyl, $R_1$'=3-fluorophenyl)

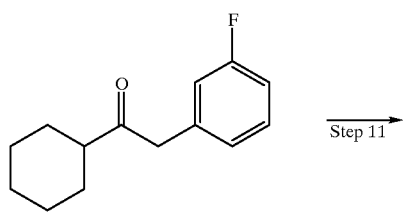

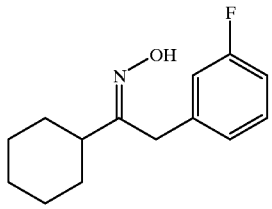

To a solution of the compound (353 g) obtained according to a method similar to that of the above Example 2, Step 10) in ethanol (1300 ml) were added hydroxylamine hydrochloride (123 g) and sodium acetate (158 g). The mixture was refluxed under heating for 2 hours, and the solvent was evaporated under reduced pressure. Ethyl acetate was added to the residue. The mixture was washed with water, saturated aqueous sodium hydrogencarbonate solution and saturated brine, and dried over anhydrous sodium sulfate. The solvent was evaporated under reduced pressure, and the crude product was recrystallized from n-heptane to give 160 g of the title compound (yield 42%).

Step 14) 4-Cyclohexyl-5-(3-fluorophenyl)-2-methyloxazole (formula (XIII); R'=cyclohexyl, $R_1$'=3-fluorophenyl, $R_2$=methyl, Z=oxygen atom)

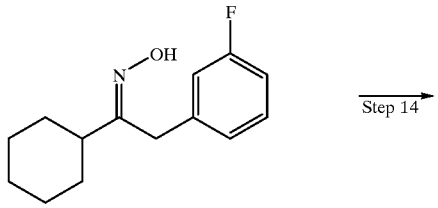

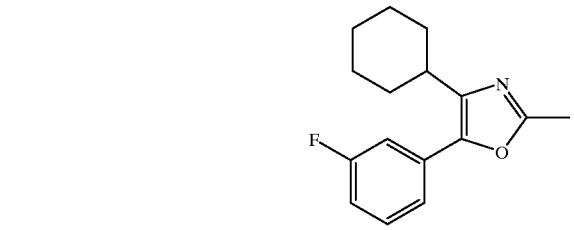

Acetic anhydride (95 ml) was dropwise added to a solution of the compound (158 g) obtained in the above Step 11) in acetic acid (900 ml) with stirring at room temperature, and the mixture was refluxed under heating for 7 hours. The solvent was evaporated under reduced pressure and n-heptane was added to the residue. The mixture was washed with water, saturated aqueous sodium hydrogencarbonate solution, saturated brine and acetonitrile. The solvent was evaporated under reduced pressure to give 119 g of the title compound as an oil.

Then, the obtained compound (119 g) was reacted in the same manner as in the above Example 2, Step 15) to give a compound of Example 2 (formula (I); R=cyclohexyl, $R_1$=4-aminosulfonyl-3-fluorophenyl, $R_2$=methyl, Z=oxygen atom).

EXAMPLE 3

Synthesis of 4-cyclohexyl-5-(3-fluoro-4-methylsulfonylphenyl)-2-methyloxazole (formula (I); R=cyclohexyl, $R_1$=3-fluoro-4-methylsulfonylphenyl, $R_2$=methyl, Z=oxygen atom)

Step 15) 4Cyclohexyl-5-(3-fluoro-4-methylsulfonylphenyl)-2-methyloxazole (formula (I); R=cyclohexyl, $R_1$=3-fluoro-4-methylsulfonylphenyl, $R_2$=methyl, Z=oxygen atom)

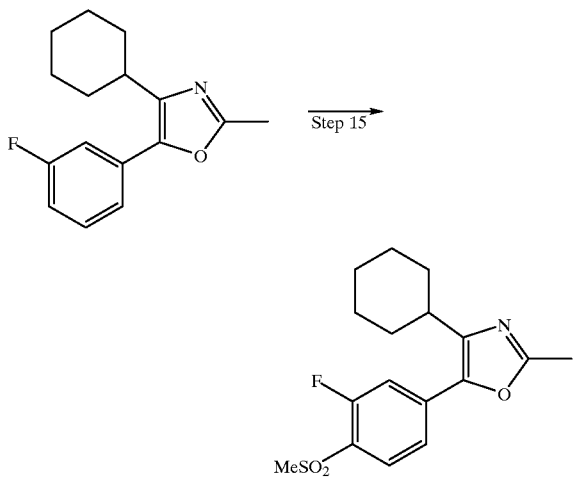

To a solution of the compound (17.00 g) obtained in the above Example 2, Step 17) in chloroform (80 ml) was dropwise added chlorosulfonic acid (27 ml) with stirring under ice-cooling. The mixture was heated at 100° C. for 3 hours. The reaction mixture was cooled to room temperature and dropwise added to ice-water (300 ml) with stirring. The organic layer was separated, washed with saturated brine, and dried over anhydrous sodium sulfate. The solvent was evaporated under reduced pressure to give 20.31 g of a crude product.

Water (25 ml) was added to the obtained compound (3.66 g). To the mixture were added sodium sulfite (1.42 g) and sodium hydrogencarbonate (1.89 g) successively with stirring at room temperature. The mixture was heated at 70° C. for 2 hours. Ethanol (25 ml) and methyl iodide (2.20 g) were added to the mixture, and the mixture was heated at 100° C. for 2 hours. The mixture was cooled to room temperature and extracted with ethyl acetate. The extract was washed with saturated brine and dried over anhydrous sodium sulfate. The solvent was evaporated under reduced pressure, and the residue was separated and purified by silica gel column chromatography (developing solvent; hexane:ethyl acetate=2:1) to give 0.82 g of the title compound (yield 24%).

EXAMPLEs 4–6

The compounds of Examples 4–6 were obtained in the same manner as in Examples 1–3 or Example 7 to be mentioned below.

The structures and properties of the compounds of Examples 1–6 are shown in the following Tables. In the Tables, Me means methyl.

TABLE 1

| Ex. | Compound | m.p. | $^1$H NMR (δ) ppm | IR cm$^{-1}$ | MS | Elem. analysis |
|---|---|---|---|---|---|---|
| 1 | [Structure: cyclohexyl-oxazole-Me with phenyl bearing MeO$_2$S and Cl] | 119~121° C. white crystals | CDCl$_3$ 300 MHz<br>1.1–1.2 (3H, m)<br>1.6–1.8 (7H, m)<br>2.48 (1H, m)<br>2.51 (3H, s)<br>3.12 (3H, s)<br>7.55 (1H, d, J = 8.1 Hz)<br>7.88 (1H, dd, J = 1.8, 8.1 Hz)<br>8.07 (1H, d, J = 1.8 Hz) | neat<br>2928<br>1578<br>1317<br>1155<br>1100<br>960 | FAB+<br>354 (MH$^+$) | |
| 2 | [Structure: cyclohexyl-oxazole-Me with phenyl bearing F and H$_2$NO$_2$S] | 166~167° C. white crystals | CDCl$_3$ 300 MHz<br>1.3–1.5 (3H, m)<br>1.6–1.9 (7H, m)<br>2.51 (3H, s)<br>2.79 (1H, tt, J = 3.7, 11.3 Hz)<br>5.11 (2H, s)<br>7.36–7.44 (2H, m)<br>7.94 (1H, t, J = 7.9 Hz) | neat<br>3280<br>2929<br>1613<br>1343<br>1170 | FAB+<br>339 (MH$^+$) | Calculated<br>C 56.79%<br>H 5.66%<br>N 8.28%<br>Found<br>C 56.41%<br>H 5.73%<br>N 8.19% |
| 3 | [Structure: cyclohexyl-oxazole-Me with phenyl bearing F and MeO$_2$S] | 111~112° C. white crystals | CDCl$_3$ 300 MHz<br>1.3–1.5 (3H, m)<br>1.6–1.8 (7H, m)<br>2.52 (3H, s)<br>2.80 (1H, tt, J = 4.0, 11.4 Hz)<br>3.25 (3H, s)<br>7.40 (1H, dd, J = 1.6, 11.2 Hz)<br>7.48 (1H, dd, J = 1.6, 8.3 Hz)<br>7.99 (1H, dd, J = 8.3, 8.4 Hz) | neat<br>2929<br>1612<br>1320<br>1161<br>1144<br>769 | FAB+<br>338 (MH$^+$) | Calculated<br>C 60.52%<br>H 5.97%<br>N 4.15%<br>Found<br>C 60.70%<br>H 6.10%<br>N 4.12% |

TABLE 2

| Ex. | Compound | m.p. | ¹H NMR (δ) ppm | IR $cm^{-1}$ | MS | Elem. analysis |
|---|---|---|---|---|---|---|
| 4 | (cyclohexyl-oxazole-Me with 2-chloro-4-aminosulfonylphenyl) | 200~201° C. white crystals | CDCl$_3$ 300 MHz<br>1.28–1.44 (4H, m)<br>1.62–1.92 (6H, m)<br>2.51 (3H, s)<br>2.72–2.83 (1H, m)<br>5.18 (2H, s)<br>7.53 (1H, dd, J = 8.4, 1.6 Hz)<br>7.69 (1H, d, J = 1.6 Hz)<br>8.13 (1H, d, J = 8.4 Hz) | KBr<br>3353<br>3255<br>2928<br>1606<br>1342<br>1166 | FAB+<br>355 (MH⁺) | Calculated<br>C 54.16%<br>H 5.40%<br>N 7.89%<br>Found<br>C 54.11%<br>H 5.45%<br>N 7.78% |
| 5 | (cyclohexyl-oxazole-Me with 2-methyl-4-aminosulfonylphenyl) | 183.2~184.2° C. white crystals | CDCl$_3$ 300 MHz<br>1.3–1.5 (3H, m)<br>1.7–1.9 (7H, m)<br>2.50 (3H, s)<br>2.73 (3H, s)<br>2.80 (1H, m)<br>4.92 (2H, s)<br>7.43–7.49 (2H, m)<br>8.05 (1H, d, J = 8.3 Hz) | KBr<br>3294<br>2929<br>1609<br>1299<br>1170 | FAB+<br>335 (MH⁺) | Calculated<br>C 61.05%<br>H 6.63%<br>N 8.38%<br>Found<br>C 61.24%<br>H 6.73%<br>N 8.43% |
| 6 | (cyclohexyl-oxazole-Me with 3,5-difluoro-4-aminosulfonylphenyl) | amorphous | CDCl$_3$ 300 MHz<br>1.28–1.47 (3H, m)<br>1.57–1.95 (7H, m)<br>2.51 (3H, s)<br>2.68–2.80 (1H, m)<br>5.37 (2H, brs)<br>7.18 (2H, ddd, J = 9.9, 1.7, 1.4 Hz) | KBr<br>2931<br>1622<br>1557<br>1422<br>1359<br>1175<br>1035 | FAB+<br>357 (MH⁺) | |

EXAMPLE 7

Synthesis of 5-(4-aminosulfonyl-3-fluorophenyl)-4-(4-fluorophenyl)-2-methyloxazole (formula (I); R=4-fluorophenyl, R$_1$=4-aminosulfonyl-3-fluorophenyl, R$_2$=methyl, Z=oxygen atom)

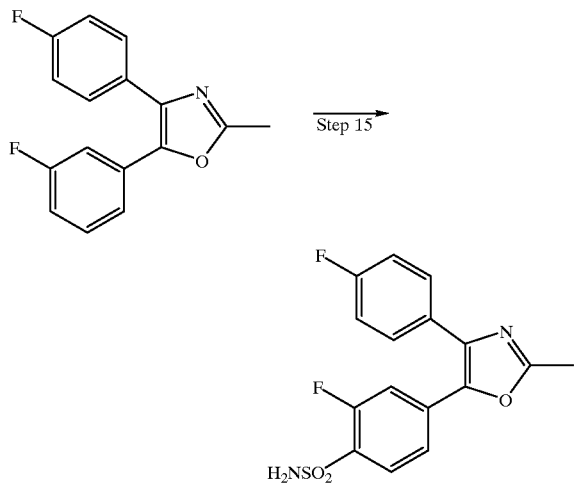

A solution of 5-(3-fluorophenyl)-4-(4-fluorophenyl)-2-methyloxazole (1.10 g) obtained by the method as mentioned above and chlorosulfonic acid (1.6 ml) in chloroform (2 ml) was heated with stirring at 90° C. for 2 hours. The reaction mixture was poured into ice-water and extracted with chloroform. The organic layer was washed with water and saturated brine, dried over anhydrous magnesium sulfate, and concentrated to give 1.06 g of a crude product of 5-(4-chlorosulfonyl-3-fluorophenyl)-4-(4-fluorophenyl)-2-methyloxazole.

To a solution of this crude product (1.06 g) in tetrahydrofuran (6 ml) was added 28% aqueous ammonia (0.6 ml) and the mixture was stirred at room temperature for 2 hours. The reaction mixture was concentrated, added with ethyl acetate, and washed with water and saturated brine. The ethyl acetate solution was dried over anhydrous magnesium sulfate, and concentrated to give 981 mg of a crude product. This crude product was recrystallized from ethanol to give 629 mg of the title compound (yield 44%). The structure and properties of this compound are shown in the following Table.

TABLE 3

| Ex. | Compound | m.p. | ¹H NMR (δ) ppm | IR cm⁻¹ | MS | Elem. analysis |
|---|---|---|---|---|---|---|
| 7 | 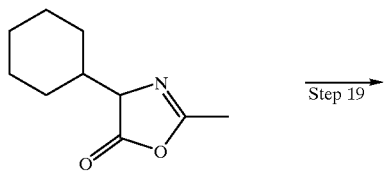 | 208° C. white crystals | CDCl₃ 300 MHz 2.58 (3H, s) 5.07 (2H, s) 7.14 (2H, tt, J = 2.2, 8.8 Hz) 7.36 (1H, dd, J = 1.5, 11.0 Hz) 7.47 (1H, dd, J = 1.8, 7.7 Hz) 7.59 (2H, ddd, J = 2.2, 5.5, 8.8 Hz) 7.88 (1H, t, J = 7.7 Hz) | neat 3278 2359 1613 1562 1510 1342 1171 | FAB+ 351 (M⁺ + 1) | Calculated C 54.74% H 3.86% N 7.66% Found C 54.40% H 3.74% N 7.59% |

EXAMPLE 2''

The compound of Example 2 (formula (I); R=cyclohexyl, $R_1$=4-aminosulfonyl-3-fluorophenyl, $R_2$=methyl, Z=oxygen atom) was synthesized according to another synthetic method.

Step 18) 4-Cyclohexyl-2-methyl-5-oxazolone (formula (XV); R'=cyclohexyl, $R_2$=methyl)

Triethylamine (8.39 ml) was added to a suspension of DL-N-acetyl-2-cyclohexylglycine (10.00 g) obtained from α-aminophenylacetic acid according to a known method [Collect. Czeck. Chem. Commun., 31: 4563 (1996)] in ethyl acetate (50 ml). Ethyl chlorocarbonate (5.28 ml) was dropwise added to the mixture under ice-cooling. The mixture was stirred under ice-cooling for one hour, added with ethyl acetate (150 ml), and washed successively with water and saturated brine. The ethyl acetate solution was concentrated under reduced pressure to give 9.86 g of the title compound as an oil.

Step 19) 4-Cyclohexyl-4-(3-fluorobenzoyl)-2-methyl-5-oxazolone (formula (XVII); R'=cyclohexyl, $R_1'$=3-fluorophenyl, $R_2$=methyl, Z=oxygen atom)

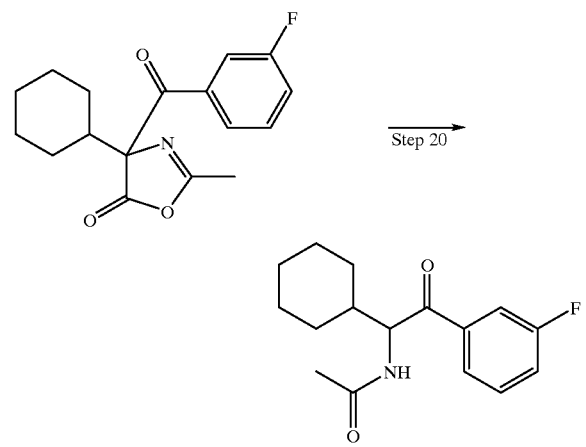

A solution of the compound (9.86 g) obtained in the above Step 18) in tetrahydrofuran (15 ml) was added to a suspension of magnesium chloride (3.56 g) in tetrahydrofuran (20 ml). Triethylamine (9.49 ml) was added with stirring under ice-cooling, and the mixture was stirred for 15 minutes. 3-Fluorobenzoyl chloride (4.55 ml) was dropwise added to the mixture, and the mixture was stirred under ice-cooling for one hour. The reaction mixture was diluted with ethyl acetate, washed with water, and dried over anhydrous sodium sulfate. The solvent was evaporated under reduced pressure to give 11.69 g of the title compound as an oil.

Step 20) 2-N-Acetylamino-2-cyclohexyl-3'-fluoroacetophenone (formula (XVIII); R'=cyclohexyl, $R_{,1}$=3-fluorophenyl, $R_2$=methyl, Z=oxygen atom)

To a solution of the compound (527 mg) obtained in the above Step 19) in tetrahydrofuran (3.5 ml) was added IN hydrochloric acid (0.35 ml). The mixture was stirred at room temperature for one hour, added with ethyl acetate, and washed successively with water, saturated aqueous sodium hydrogencarbonate solution and saturated brine. The organic layer was dried over anhydrous sodium sulfate, and the solvent was evaporated under reduced pressure to give 404 mg of the title compound as a solid (yield 84%). The solid was recrystallized from n-heptane to give white crystals, melting point 116–117° C.

Step 21) 5-(4-Aminosulfonyl-3-fluorophenyl)-4-cyclohexyl-2-methyloxazole (formula (I); R=cyclohexyl, R$_1$=4-aminosulfonyl-3-fluorophenyl, R$_2$=methyl, Z=oxygen atom)

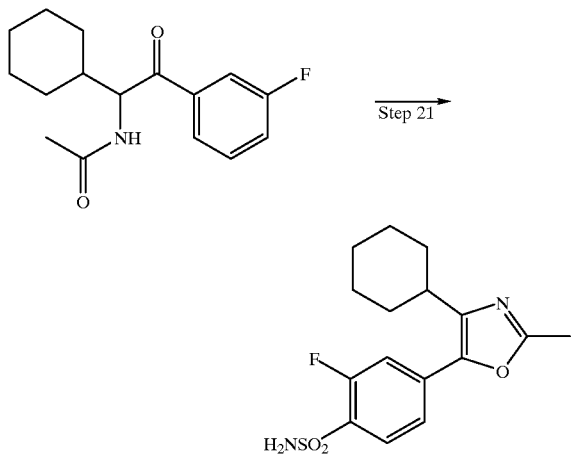

Chlorosulfonic acid (0.34 ml) was added to a solution of the compound (200 mg) obtained in the above Step 20) in chloroform (2 ml) with stirring under ice-cooling, and the mixture was refluxed under heating for 5 hours. The reaction mixture was diluted with chloroform and poured into ice-water. The organic layer was separated, washed successively with water and saturated brine, and dried over anhydrous sodium sulfate. The solvent was evaporated under reduced pressure to give 181 mg of a crude product.

To a solution of the obtained compound (169 mg) in tetrahydrofuran (2 ml) was added 28% aqueous ammonia (0.1 ml) with stirring at room temperature, and the mixture was stirred for 30 minutes. The solvent was evaporated under reduced pressure. Ethyl acetate was added to the residue, and the mixture was washed successively with water and saturated brine, which was followed by drying over anhydrous sodium sulfate. The solvent was evaporated, and the residue was separated and purified by silica gel column chromatography (developing solvent; dichloromethane:ethyl acetate=6:1) to give 126 mg of the title compound (yield 55%).

EXAMPLE 2'''

The compound of Example 2 (formula (I); R=cyclohexyl, R$_1$=4-aminosulfonyl-3-fluorophenyl, R$_2$=methyl, Z=oxygen atom) was synthesized according to another synthetic method.

Step 22) 4-Cyclohexyl-5-(3-fluorophenyl)-2-methyloxazole (formula (XIII); R'=cyclohexyl, R$_1$'=3-fluorophenyl, R$_2$=methyl)

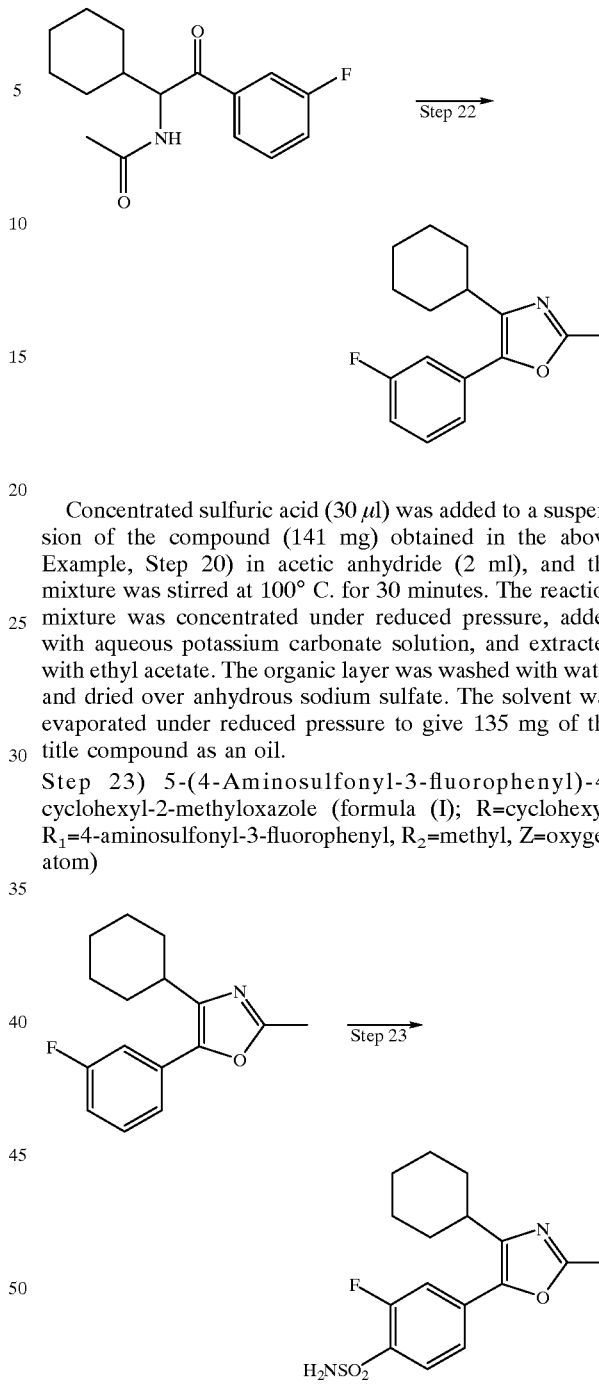

Concentrated sulfuric acid (30 µl) was added to a suspension of the compound (141 mg) obtained in the above Example, Step 20) in acetic anhydride (2 ml), and the mixture was stirred at 100° C. for 30 minutes. The reaction mixture was concentrated under reduced pressure, added with aqueous potassium carbonate solution, and extracted with ethyl acetate. The organic layer was washed with water and dried over anhydrous sodium sulfate. The solvent was evaporated under reduced pressure to give 135 mg of the title compound as an oil.

Step 23) 5-(4-Aminosulfonyl-3-fluorophenyl)-4-cyclohexyl-2-methyloxazole (formula (I); R=cyclohexyl, R$_1$=4-aminosulfonyl-3-fluorophenyl, R$_2$=methyl, Z=oxygen atom)

In the same manner as in the above Example 2, Step 15), the compound obtained in the above Step 22) was reacted to give the compound of Example 2 (formula (I); R=cyclohexyl, R$_1$=4-aminosulfonyl-3-fluorophenyl, R$_2$=methyl, Z=oxygen atom).

Experimental Example 1 (Inhibitory Action on Cyclooxygenase)

The enzymatic activity was determined from the percent conversion of $^{14}C$ arachidonic acid into prostaglandin H$_2$ (PGH$_2$) and the decomposed product thereof. That is, a test sample (20 μl), an enzyme solution (20 μl) and distilled water (10 μl) were added to 100 mM Tris-HCl buffer (pH 8, 140 μl) containing hematin (2 μM) and tryptophan (5 mM), and the mixture was thoroughly stirred, which was followed by preincubation at 24° C. for 5 minutes. Then, a $^{14}$C arachidonic acid solution (10 μl) was added and the mixture was reacted at 24° C., whereafter a solution (40 μl) of ethyl ether/methanol/1M citric acid (30/4/1) iceooled to −20° C. was added to stop the reaction. The reaction mixture was centrifuged for 5 minutes at 3,000 rpm to give an ether layer which was placed on a thin plate, and developed with ethyl ether/methanol/acetic acid (90/2/0.1) to determine percent conversion (A) from arachidonic acid to $PGH_2$ and the decomposed product thereof. The percent conversion (B) without a test sample was also determined, based on which percent inhibition was calculated from the following formula, and a concentration ($IC_{50}$) necessary for 50% inhibition of the test sample was determined.

Inhibition (%)=(1A/B)×100

An enzyme prepared from human platelets was used as an enzyme solution of cyclooxygenase-1, and an enzyme expressed by a yeast, into which cDNA of human cyclooxygenase-2 had been introduced using a kit of Invitrogen Corp., was used as an enzyme solution of cyclooxygenase-2. As used herein, control compound 1 was 5-(4-aminosulfonylphenyl)-4-cyclohexyl-2-methyloxazole, a patent application to which has been previously filed by us, and control compound 2 was a known analogous compound, 5-(4-aminosulfonylphenyl)-4-(4-fluorophenyl)-2-methyloxazole.

The results are shown in Table 4.

As is evident from the comparison of control compound 1 and the compound of Example 2, as well as control compound 2 and the compound of Example 7, a remarkable reduction of the action on COX-1 while retaining the activity on COX-2 has become possible particularly by introducing fluorine atom.

TABLE 4

| | Experimental Example 1 (inhibitory action on cyclooxygenase) | | | |
| --- | --- | --- | --- | --- |
| Example | Structural formula | $IC_{50}$ (μM) | | |
| | | COX-2 | COX-1 | COX-1/COX-2 |
| 2 | | 0.07 | >100 | >1,428 |
| 3 | | 0.3 | >100 | >333 |
| 4 | | >10 | | |

TABLE 4-continued

Experimental Example 1 (inhibitory action on cyclooxygenase)

| Example | Structural formula | IC$_{50}$ ($\mu$M) COX-2 | COX-1 | COX-1/COX-2 |
|---|---|---|---|---|
| 5 | (structure: 4-cyclohexyl-5-(3-methyl-4-sulfamoylphenyl)-2-methyloxazole) | >10 | | |
| 6 | (structure: 4-cyclohexyl-5-(3,5-difluoro-4-sulfamoylphenyl)-2-methyloxazole) | 0.16 | >100 | >625 |
| 7 | (structure: 4-(4-fluorophenyl)-5-(3-fluoro-4-sulfamoylphenyl)-2-methyloxazole) | 0.03 | 37 | 1,233 |
| Indomethacin | | 8 | 0.5 | 0.063 |
| Control 1 | (structure: 4-cyclohexyl-5-(4-sulfamoylphenyl)-2-methyloxazole) | 0.07 | 45 | 643 |
| Control 2 | (structure: 4-(4-fluorophenyl)-5-(4-sulfamoylphenyl)-2-methyloxazole) | 0.02 | 5 | 250 |

Experimental Example 2 (effects on carrageen in induced podedema) Carrageenin (1%, 0.05 ml) dissolved in physiological saline was subcutaneously injected to the left hind-limb of male Donryu rats to induce podedema. The degree of podedema was evaluated by measuring the volume of the limb 3 hours after carrageenin administration. A test compound (1, 3, 10 or 30 mg/kg) was orally administered one hour before carrageenin administration, and suppression thereby was studied. Inhibitory activity was expressed by the dose (ED30) of the test compound necessary for inhibiting by 30% relative to the control group. The results are shown in Table 5.

TABLE 5

Experimental Example 2
(effects on carrageenin-induced podedema in rats)

| Example | carrageenin-induced podederna in rats, $ED_{30}$ (mg/kg p.o.) |
|---|---|
| 2 | 5.5 |
| indomethacin | 2.9 |

INDUSTRIAL APPLICABILITY

The compound of the present invention, in particular, a compound wherein $R_3$ is methyl or amino, Rs is fluorine atom, RG is hydrogen atom or fluorine atom, and Rt and R. are hydrogen atom, and pharmaceutically acceptable salts thereof surprisingly selectively inhibit COX-2 alone, while scarcely inhibiting COX-1. Accordingly, the compound of the present invention possesses superior antipyretic action, analgesic action and anti-inflammatory action that the conventional products cannot afford, and scarcely show side-effects in the digestive tract.

Consequently, the development of a superior anti-inflammatory agent heretofor not existed has been enabled, which in turn produces great expectation of the provision of a practical therapeutic agent for the diseases possibly caused by COX-2 product, such as asthma and rheumatism.

What is claimed is:

1. A compound of the formula (I):

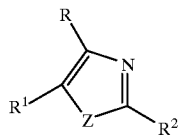

(I)

wherein

Z is oxygen;

one of R and $R^1$ is a group of the formula

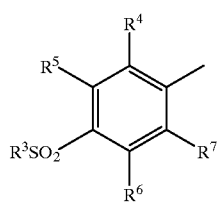

wherein $R^3$ is a $C_{1-4}$ alkyl, amino, or $C_{1-4}$ alkylamino, and $R^4$, $R^5$, $R^6$, and $R^7$ are the same or different and each is hydrogen or fluorine provided that at least one of $R^4$, $R^5$, $R^6$, and $R^7$ is not hydrogen, and the other of R and $R^1$ is (i) selected from the group consisting of phenyl, naphthyl, biphenyl, $C_{5-7}$ cycloalkyl, thienyl, furyl, and pyrrolyl, and is (ii) unsubstituted or substituted by 1 to 3 substituents selected from the group consisting of hydroxy, $C_{1-4}$ alkyl, $C_{1-4}$ alkoxy, mercapto, $C_{1-4}$ alkylthio, halogen, trifluoromethyl, $C_{1-4}$ alkylcarbonyl, $C_{1-4}$ alkoxycarbonyl, acetamido, and propionylamido; and $R^2$ is $C_{1-4}$ alkyl;

or a pharmaceutically acceptable salt thereof.

2. A compound as claimed in claim 1, wherein:

$R^1$ is a group of the formula

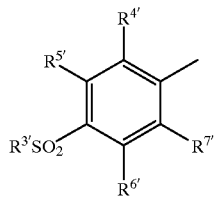

wherein $R^{3'}$ is a $C_{1-4}$ alkyl or amino, and $R^{4'}$, $R^{5'}$, $R^{6'}$, and $R^{7'}$ are the same or different and each is hydrogen or fluorine provided that at least one of $R^{4'}$, $R^{5'}$, $R^{6'}$, and $R^{7'}$ is not hydrogen, and $R^2$ is methyl;

or a pharmaceutically acceptable salt thereof.

3. A compound as claimed in claim 1, wherein:

$R^1$ is a group of the formula

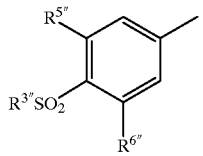

wherein $R^{3''}$ is a methyl or amino, $R^{5''}$ is fluorine, and $R^{6''}$ is hydrogen or fluorine, and $R^2$ is methyl;

or a pharmaceutically acceptable salt thereof.

4. A compound as claimed in claim 3, wherein

R is a $C_{5-7}$ cycloalkyl or phenyl which is unsubstituted or substituted by 1 to 3 substituents selected from the group consisting of hydroxy, $C_{1-4}$ alkyl, $C_{1-4}$ alkoxy, mercapto, $C_{1-4}$ alkylthio, halogen, trifluoromethyl, $C_{1-4}$ alkylcarbonyl, $C_{1-4}$ alkoxycarbonyl, acetamido, and propionplamido;

or a pharmaceuticall y acceptable salt thereof.

5. A compound as claimed in claim 4, wherein

R is cyclohexyl or 4-fluorophenyl, and $R^1$ is 4-aminosulfonyl-3-fluorophenyl, 4-aminosulfonyl-3,5-difluorophenyl, 3-fluoro-4-methylsulfonylphenyl or 3,5-difluoro-4-methylsulfonylphenyl;

or a pharmaceutically acceptable salt thereof.

6. A compound as claimed in claim 1, which is 4-cyclohexyl-5-(3-fluoro-4-methylsulfonylphenyl)-2-methyloxazole, 5-(4-aminosulfonyl-3-fluorophenyl)-4-cyclohexyl-2-methyloxazole, 5-(4-aminosulfonyl-3,5-difluorophenyl)-4-cyclohexyl-2-methyloxazole, 4-cyclohexyl-5-(3,5-difluoro-4-methylsulfonylphenyl)-2-methyloxazole, or 5-(4-aminosulfonyl-3-fluorophenyl)-4-(4-fluorophenyl)-2-methyloxazole, or a pharmaceutically acceptable salt thereof.

7. A pharmaceutical composition comprising a therapeutically effective amount of a compound as claimed in claim 1, or a pharmaceutically acceptable salt thereof, and a pharmaceutically acceptable carrier.

8. A method for treating an inflammatory disease, comprising administering to a subject in need thereof a pharmaceutical composition as claimed in claim 7.

* * * * *